United States Patent
Nakamura et al.

[11] Patent Number: 6,140,077
[45] Date of Patent: Oct. 31, 2000

[54] METHOD FOR PRODUCING PHYTASE

[75] Inventors: Takeshi Nakamura, Ichihara; Tadashi Suzuki, Chiba; Junko Tokuda, Mobara; Nobuo Kato, Kameoka; Yasuyoshi Sakai, Otsu; Daisuke Mochizuki, Narita; Hitoshi Takahashi, Takikawa, all of Japan

[73] Assignee: Mitsui Chemicals, Inc., Japan

[21] Appl. No.: 09/014,583

[22] Filed: Jan. 28, 1998

[51] Int. Cl.$^7$ .......................... C12P 21/06; C12N 15/00; C12N 9/16; C12N 1/14

[52] U.S. Cl. ................ 435/69.1; 435/320.1; 435/254.22; 435/196

[58] Field of Search ................. 435/69.1, 320.1, 435/254.22, 196

[56] References Cited

U.S. PATENT DOCUMENTS 5,750,372   5/1998   Sakai et al. ............................ 435/69.1

FOREIGN PATENT DOCUMENTS

| | | |
|---|---|---|
| 0 101 273 A2 | 2/1984 | European Pat. Off. |
| 0 558 024 | 9/1993 | European Pat. Off. |
| 0 699 762 | 3/1996 | European Pat. Off. |
| 0699762A2 | 3/1996 | European Pat. Off. |
| WO 97/48812 | 12/1997 | WIPO |

OTHER PUBLICATIONS

Sakai, Y. et al., Appl. Microbiol. Biotechnol., vol. 42, pp. 860–864, 1995.
Sakai, Y. et al., Appl. Environ. Microbiol., vol. 53, No. 8, pp. 1812–1818, Aug. 1987.
Egli, T. et al., J. Gen. Microbiol., vol. 123, p. 365–369, 1981.
XP–002067635, Chemical Abstracts 164352d, vol. 128, No. 14.
XP–002067634, Abstract of the Paper of the 196$^{th}$ Meeting of the American Chemical Society, p. mbtd105.

*Primary Examiner*—Ponnathapu Achutamurthy
*Assistant Examiner*—Peter P. Tung
*Attorney, Agent, or Firm*—Burns, Doane, Swecker & Mathis, L.L.P.

[57] ABSTRACT

A method for producing phytase using a *Candida boidinii* transformant, by which phytase is secreted to liquid medium without substantially increasing the number of the transformant cells is disclosed. In this method, cells of a *Candida boidinii* transformant which is transformed with a recombinant vector comprising a promoter inducible with methanol and a gene located downstream of said promoter and operably linked to said promoter, which gene encodes a polypeptide having phytase activity, are cultured in a liquid culture medium containing phosphoric acid or a phosphate compound in an amount effective of restricting proliferation of said cells of *Candida boidinii* transformant such that the amount of said cells of *Candida boidinii* transformant is not substantially increased, while adding methanol to the culture medium, so as to make said cells secrete said phytase.

12 Claims, 2 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 734 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Candida boidinii
      (D) DEVELOPMENTAL STAGE: wild type (xi) SEQUENCE DESCRIPTION: SEQ ID NO:1:

```
TCTAGAATTT CATTATTTAT TTTTTATTGA CTGGAAATTT TCAATCAATT TTATTTATTT      60

TTATTTATTT ATTTTCATAT TCTTAGATTT AAACTTTTTA GATGACCGCT ATTTTACTTA     120

CTTACTTACT TACTTACTTA CTTACTTACT TACATACCTA CTTACTGTGA TTTTATAATA     180

TGATAAGAAT TAATTTTCAT ATTTATGATG ATGTAAATTT AACCTAGTAT ACTATTTTAA     240

AGTTATCACT ATCTTTTAGT GCTGGCATTT TTTATTCTAT TTTCATATAT GTATATAAGT     300

AAATTAAGTA TCATCACGCT GCTTACTGTA CGTTTAAAAT GTGGAGATGG AAATAGAGAT     360

GGGGATGAAG ATGAAGATGA TGAGAATTAT AAACCATTCA TTCATTAATC AATCAATATA     420

ACTTATAAAA AAATTTATAT TTAAATGAAT TAATTTCCTT TATTTTAATA ATATCGTTAA     480
```

-continued

```
TTCTTTTAAA TTCTATTTTA TTTTAATTCT TTCTTTATCA TAGTTATCAT ATAACAATTA      540

TATAACATAG ATACACAATT ATTATTTTAT TATCATATTA TTTTTTAAAA TATTGATTAT      600

TTTTAAAATA ATATCTTAAT TAATTAATTT TTACGAATAT ACAAATTTTA ACGACTTTCT      660

TTTTTTAACG AATTTTAACG AACTTTTAAA AAAACAAAAA AAAAAAAACA AAATTATTTT      720

TCAATAGCGG CCGC                                                        734
```

(2) INFORMATION FOR SEQ ID NO:2:

(i) SEQUENCE CHARACTERISTICS:
        (A) LENGTH: 1631 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Schwanniomyces occidentalis
        (D) DEVELOPMENTAL STAGE: wild type (ix) FEATURE:
        (A) NAME/KEY: CDS
        (B) LOCATION: 8..1393

(xi) SEQUENCE DESCRIPTION: SEQ ID NO:2:

```
GTCAATC ATG GTC TCG ATC TCA AAA TTA ATT AAT AAC GGT TTA CTC TTA         49
        Met Val Ser Ile Ser Lys Leu Ile Asn Asn Gly Leu Leu Leu
         1               5                  10

GCT GGT CAA AGT GTT TAC CAA GAT TTA GCT ACT CCA CAA CAA TCT TCC         97
Ala Gly Gln Ser Val Tyr Gln Asp Leu Ala Thr Pro Gln Gln Ser Ser
 15              20                  25                  30

GTC GAG CAG TAT AAT ATT ATT AGG TTT TTA GGT GGT TCG GGT CCT TAC        145
Val Glu Gln Tyr Asn Ile Ile Arg Phe Leu Gly Gly Ser Gly Pro Tyr
                 35                  40                  45

ATT CAA CGC AGT GGT TAT GGT ATT TCC ACT GAT ATT CCT GAT CAG TGC        193
Ile Gln Arg Ser Gly Tyr Gly Ile Ser Thr Asp Ile Pro Asp Gln Cys
                 50                  55                  60

ACA ATT AAG CAA GTT CAG TTG ATG TCA AGG CAT GGG GAA AGA TAC CCT        241
Thr Ile Lys Gln Val Gln Leu Met Ser Arg His Gly Glu Arg Tyr Pro
 65                  70                  75

TCA AAA AAC TCT GGT AAG AAG TTA AAA ACA ATA TAT GGT AAA TTA AAG        289
Ser Lys Asn Ser Gly Lys Lys Leu Lys Thr Ile Tyr Gly Lys Leu Lys
 80                  85                  90

AGC TAC AAT GGC ACT TTC ACA GGT AGC TTA GCT TTT TTG AAT GAC TAT        337
Ser Tyr Asn Gly Thr Phe Thr Gly Ser Leu Ala Phe Leu Asn Asp Tyr
 95                 100                 105                 110

GAA TAT TTT GTT CCG GAT GAT AGT TTG TAC GAA AAG GAA ACA AGT GCA        385
Glu Tyr Phe Val Pro Asp Asp Ser Leu Tyr Glu Lys Glu Thr Ser Ala
                115                 120                 125

CTG AAC TCG CAA GGT TTA TTT GCA GGT ACT ACA GAT GCC TTA AGA CAT        433
Leu Asn Ser Gln Gly Leu Phe Ala Gly Thr Thr Asp Ala Leu Arg His
                130                 135                 140

GGT GCT GCT TTT AGA GCT AAA TAT GGA TCA TTG TAT AAA CAA AAT TCT        481
Gly Ala Ala Phe Arg Ala Lys Tyr Gly Ser Leu Tyr Lys Gln Asn Ser
                145                 150                 155

ACC TTG CCA GTT TTC ACT TCA AAT TCC AAC AGA GTC TAC CAG ACT TCT        529
Thr Leu Pro Val Phe Thr Ser Asn Ser Asn Arg Val Tyr Gln Thr Ser
 160                 165                 170

GAA TAC TTT GCC AGA GGT TTC TTA GGT GAT GAA TTT TCT GAT GCT ACT        577
Glu Tyr Phe Ala Arg Gly Phe Leu Gly Asp Glu Phe Ser Asp Ala Thr
 175                 180                 185                 190
```

-continued

```
GTT CAC TTT GCT ATC ATT GAT GAA GAC CCT AAA ATG GGT GTT AAT TCA          625
Val His Phe Ala Ile Ile Asp Glu Asp Pro Lys Met Gly Val Asn Ser
            195                 200                 205

TTA ACA CCA AGA GCC GCT TGT GAC AAT TAT AAT GAG GAT GTG AAT GAC          673
Leu Thr Pro Arg Ala Ala Cys Asp Asn Tyr Asn Glu Asp Val Asn Asp
                210                 215                 220

GGC ATT GTC AAT CAA TAT AGC ACT GAC TAT TTG GAT GAA GCC CTT AAA          721
Gly Ile Val Asn Gln Tyr Ser Thr Asp Tyr Leu Asp Glu Ala Leu Lys
                225                 230                 235

AGA TTC CAA TCA TCA AAT CCA GGA TTG AAT TTG ACC TCG GAA GAC GTT          769
Arg Phe Gln Ser Ser Asn Pro Gly Leu Asn Leu Thr Ser Glu Asp Val
    240                 245                 250

TAC CAA CTT TTC GCT TAC TGT GCA TAT GAG ACT AAT GTT AAG GGT GCA          817
Tyr Gln Leu Phe Ala Tyr Cys Ala Tyr Glu Thr Asn Val Lys Gly Ala
255                 260                 265                 270

TCC CCA TTC TGT GAC TTA TTT ACT AAT GAA GAA TAC ATT CAA TAT TCC          865
Ser Pro Phe Cys Asp Leu Phe Thr Asn Glu Glu Tyr Ile Gln Tyr Ser
                275                 280                 285

TAC AGC GTT GAT CTT TCT AAT TAT TAT TCT CAC GGG GCA GGT CAT AAT          913
Tyr Ser Val Asp Leu Ser Asn Tyr Tyr Ser His Gly Ala Gly His Asn
                290                 295                 300

CTA ACT AAA ACC ATT GGT TCT ACT TTA TTA AAT GCC TCA TTA ACC TTA          961
Leu Thr Lys Thr Ile Gly Ser Thr Leu Leu Asn Ala Ser Leu Thr Leu
            305                 310                 315

TTA AAA GAT GGC ACC AAT GAC AAT AAA ATC TGG TTA TCT TTT TCA CAC         1009
Leu Lys Asp Gly Thr Asn Asp Asn Lys Ile Trp Leu Ser Phe Ser His
    320                 325                 330

GAT ACT GAT TTG GAA ATC TTC CAT AGT GCC TTA GGA ATT GTT GAG CCA         1057
Asp Thr Asp Leu Glu Ile Phe His Ser Ala Leu Gly Ile Val Glu Pro
335                 340                 345                 350

GCT GAA GAT TTA CCA GTT GAT TAC ATT CCT TTT CCA TCG CCA TAT ATT         1105
Ala Glu Asp Leu Pro Val Asp Tyr Ile Pro Phe Pro Ser Pro Tyr Ile
                355                 360                 365

CAC TCA CAA ATT GTT CCA CAA GGT GCT AGA ATT TAT ACT GAG AAA TAT         1153
His Ser Gln Ile Val Pro Gln Gly Ala Arg Ile Tyr Thr Glu Lys Tyr
                370                 375                 380

TCA TGT GGC AAC GAA ACC TAT GTT AGA TAT ATA CTT AAT GAT GCA GTT         1201
Ser Cys Gly Asn Glu Thr Tyr Val Arg Tyr Ile Leu Asn Asp Ala Val
            385                 390                 395

GTT CCA ATT CCA AAA TGC TCT TCT GGT CCA GGG TTC TCA TGT GAG CTT         1249
Val Pro Ile Pro Lys Cys Ser Ser Gly Pro Gly Phe Ser Cys Glu Leu
    400                 405                 410

AGT AAA TTC GAA GAA TAT ATT AAT AAA AGA CTT AGG GAT GTT GAC TTT         1297
Ser Lys Phe Glu Glu Tyr Ile Asn Lys Arg Leu Arg Asp Val Asp Phe
415                 420                 425                 430

GTT GAA CAA TGT GAT TTA AAA GAT GCT CCA ACT GAA GTT ACT TTT TAC         1345
Val Glu Gln Cys Asp Leu Lys Asp Ala Pro Thr Glu Val Thr Phe Tyr
                435                 440                 445

TGG GAT TAC ACG TCG GTG AAC TAT AGT GCG TCC CTT ATT AAT GGT TAA         1393
Trp Asp Tyr Thr Ser Val Asn Tyr Ser Ala Ser Leu Ile Asn Gly  *
                450                 455                 460

ATTGAGTATA GGAGAATATC TTATTTCTAG TTTGATCACT ATCTGAATCC ACTTTGCTCT       1453

TTCTCCTTGT TTTGATTGCT TATCCATTGT TTAGAAATAC GTTATAAAGC AATCATTTTT       1513

ACAACTATGT CGTCTAATAC TTTGTTTCTA GAATTAAAAA AATAAATAGT ATACCTGTGT       1573

AAAGTCTTAC TTGATAGCTA ACTAGTCACT TCTTAATCAT ACACCTAATC TATCCTAA        1631
```

METHOD FOR PRODUCING PHYTASE

BACKGROUD OF THE INVENTION

I. Field of the Invention

The present invention relates to a method for producing phytase, as well as to recombinant vector and a transformant used in the method.

II. Description of the Related Art

Phytase is an enzyme which hydrolyzes phytin to produce phosphate. In recent years, it is tried to decrease the phosphate level in feces of livestock by adding phytase to the feed of livestock as an additive so as to decompose phytin which cannot be digested by monogastric animals such as chicken and pig, thereby effectively utilize the phosphate in the feed.

EP-A-0 699 762 discloses phytase and a gene coding for the phytase originated from *Schwaniiomyces occidentalis*. This phytase can hydrolyze phytic acid to myo-inositol and has an excellent thermal stability. Thus, since the phytase is not likely to be inactivated even if the phytase contained in feed is exposed to high temperature during preparation process of the feed, this phytase is industrially useful.

EP-A-0 699 762 discloses a process for producing phytase by transformant of yeast *Saccharomyces cerevisiae*. However, the process may be further improved with respect to secretionary production of the phytase.

Incidentally, among the production processes of a recombinant protein by using a recombinant microorganism, production of the recombinant protein by making cells of the recombinant microorganism secrete the recombinant protein to the outside of the cells is desired because feedback regulation is likely to be turned off, the produced recombinant protein is likely not to be decomposed and so is likely to be recovered in active form, and purification of the obtained recombinant protein is easy.

On the other hand, to stably produce the recombinant protein, it is preferred that the recombinant microorganism be a yeast since cultivation of yeasts is easy and the gene encoding the recombinant protein, which gene is introduced in the yeast, can be incorporated into the chromosome of the yeast. Because of this, secretionary productions of recombinant proteins using recombinant yeasts have been studied. However, secretionary production of recombinant proteins by yeasts, especially when the recombinant proteins are originated from a species other than the yeast, the secretionary production efficiencies are lower than those by bacteria such as *Bacillus subtilis*.

References disclosing secretionary production of a recombinant protein with high yield include EP-A-0 558 024, EP-A-0 794 256 and Y. Sakai et al., Biochim. Biophys. Acta Vol.1308, pp.81–87, (1996).

EP-A-0 558 024 discloses an expression cassette comprising the promoter and terminator of alcohol oxidase (AOD) gene of *Candida boidinii*; an expression vector having the expression cassette, and a transformed yeast having the expression vector. This patent publication specifically discloses expression of adenylate kinase, cytochrome C 552 and a peroxidase using the expression cassette.

In EP-A-0 794 256, a transformed yeast (*Candida boidinii*) having a recombinant plasmid obtained by inserting a gene encoding a polypeptide originated from *Saccharomyces cerevisiae* Kex2 protease into the above-mentioned expression vector is prepared, and the polypeptide originating from Kex2 protease is produced by culturing the transformed yeast while adding methanol to the liquid medium in which the yeast transformant cells are cultured.

Sakai et al. produced glucoamylase originated from *Rhizopus oryzae* by culturing a transformant of *Candida boidinii* which is a methanol-assimilating yeast while adding methanol, glycerol and concentrate of the components of the culture medium, thereby accumulating the glucoamylase to a level of 3.4 g/l.

In these known processes, although the desired protein or polypeptide is produced in a large amount, the amount of the microorganism cells is also increased with the production of the desired product. This means that the production efficiency per a unit amount of microorganism cells is decreased with time, so that the production process is not very efficient.

Further, the present inventors discovered that *Candida boidinii* secretes a kind of viscous polysaccharide to the outside of the cells. By increase in the cell concentration of the yeast cells during culture, the polysaccharide secreted by the yeast cells accumulates in the culture medium, so that the viscosity of the culture medium is increased. Consequently, it comes to be difficult to supply sufficient oxygen to the yeast cells, so that the desired recombinant protein cannot be produced well.

Further, if the microorganism cells are too much increased, purification of the desired product is difficult, and the cost for disposing the wasted cells is increased. Therefore, in industrial processes, it is not desired to too much increase the number of microorganism cells.

Thus, it is desired to develop a fed-batch culture method by which a desired product is stably and continuously produced efficiently for a long time while restricting the growth of the microorganism to a certain level. However, for secretionary production of recombinant proteins using yeasts, such a fed-batch culture method is not known. Even a process for secretionary production wherein the recombinant protein is phytase is not known at all.

SUMMARY OF THE INVENTION

Accordingly, an object of the present invention is to provide a novel and efficient method for secretionary production of phytase by culturing a recombinant *Candida boidinii* in a liquid medium so as to make the yeast cells continuously secrete the phytase, without substantially increasing the amount of the yeast cells.

The present inventors intensively studied to discover that by culturing *Candida boidinii* transformant cells containing a recombinant vector having a promoter inducible with methanol, and a gene encoding phytase downstream of the promoter in the presence of an amount of phosphoric acid or a phosphate compound, at which growth of the yeast is restricted, the phytase can be secreted by the cells without substantially increasing the number of the cells, thereby completing the present invention.

That is, the present invention provides a method for producing a polypeptide having phytase activity comprising culturing cells of a *Candida boidinii* transformant which is transformed with a recombinant vector comprising a promoter inducible with methanol and a gene located downstream of the promoter and operably linked to the promoter, which gene encodes a polypeptide having phytase activity, in a liquid culture medium containing phosphoric acid or a phosphate compound in an amount at which proliferation of the cells of *Candida boidinii* transformant is restricted such that the number of the cells of *Candida boidinii* transformant is not substantially increased, while adding methanol to the culture medium, so as to make the cells secrete the polypeptide. The present invention also provides a recombinant vector comprising a promoter inducible with methanol and a gene located downstream of the promoter and operably linked to the promoter, which gene encodes a polypeptide having phytase activity, which recombinant vector is capable of expressing the gene in a host cell. The present invention further provides a *Candida boidinii* transformant which is transformed with the recombinant vector according to the present invention.

By the method of the present invention, phytase can be produced in a large amount efficiently. According to the method of the present invention, since the cell concentration is not increased to more than a certain level, the production of phytase per a unit amount of cells is high. Further, since production of phytase is continued for a long time without accompanying substantial increase in the amount of the cells, rate of production of phytase is high, the components of the medium are effectively used, and the purification step is not troublesome. Therefore, the method of the present invention is useful as a method for industrially producing phytase.

DETAILED DESCRIPTION OF THE PREFERRED EMBODIMENTS

Figure 1:
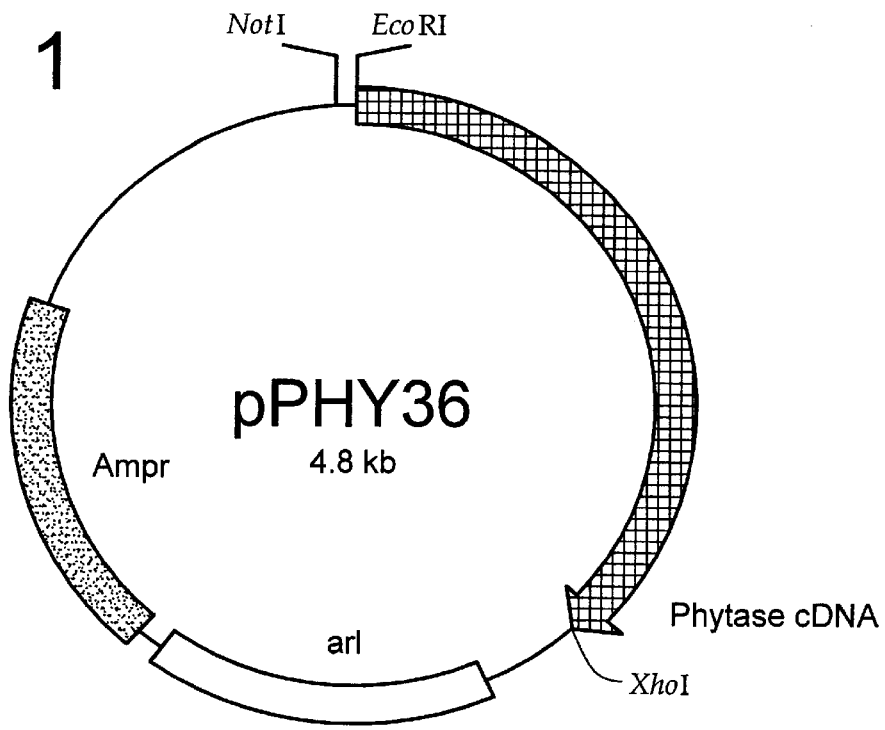
FIG. 1 shows the structure of a plasmid PHY36 containing the cDNA of phytase originated from *Schwaniiomyces occidentalis;*

The promoter employed in the present invention may be any nucleic acid sequence having promoter activity, which is inducible with methanol. Preferred promoters are those originated from methanol oxidase of methanol-assimilating yeasts, such as the promoter of AOD1 gene of *Candida boidinii* (EP-A-0 558 024), the promoter of AOX1 or AOX2 gene of *Pichia pastoris* (J. M. Cregg et al., Mol. Cell. Biol. 5: pp. 3376–3385 (1985)), and the promoter of MOX gene of *Hansenula polymorpha* (P. E. Sudbery et al., Biochem. Soc. Trans. 16: pp.1081–1083 (1988)). Among these, the AOD1 promoter of *Candida boidinii* is best preferred. A nucleotide sequence including the AOD1 promoter is shown in SEQ ID NO. 1 in the Sequence Listing. It should be noted that a part of the sequence shown in SEQ ID NO. 1 which has a promoter activity can be utilized. Further, a promoter sequence having a nucleotide sequence homologous to the sequence shown in SEQ ID NO. 1 or a part thereof may also be employed as long as it has a promoter activity and is induced by methanol. Especially, a sequence having a homology of not less than 70%, preferably not less than 90% to the sequence shown in SEQ ID NO. 1 or a sequence which can hybridize with the sequence shown in SEQ ID NO. 1 under stringent condition (hybridization condition: in 5×SSC, 50% formamide, 0.1% SDS at 42° C. for 12 hours; washing condition: 0.1×SSC, 0.1% SDS, 68° C., 15 min.) may be employed as long as it has a promoter activity and is induced by methanol.

The gene encoding a polypeptide having phytase activity may be any nucleic acid which encodes a polypeptide having an activity to hydrolyze phytic acid, which is expressed in the host *Candida boidinii* when operably ligated to a site downstream of the promoter and which enables the host cells to secrete the polypeptide to the outside of the cells. A preferred example of such a gene is the phytase gene originated from *Schwanniomyces occidentalis* (EP-A-0 699 762), of which nucleotide sequence and the amino acid sequence encoded thereby are shown in SEQ ID NO. 2. It should be noted that a part of the sequence shown in SEQ ID NO. 2 which encodes a polypeptide having phytase activity can also be utilized. Further, a gene having a nucleotide sequence different from that shown in SEQ ID NO. 2 but encodes the same amino acid sequence as shown in SEQ ID NO. 2 may also be employed. Still further, a gene having a nucleotide sequence homologous to the sequence shown in SEQ ID NO. 2 or a part thereof may also be employed as long as the polypeptide encoded thereby has phytase activity. Especially, a sequence having a homology of not less than 70%, preferably not less than 90% to the sequence shown in SEQ ID NO. 2 (especially the region of 8 nt to 1390 nt encoding the protein) or a sequence which can hybridize with the coding region of 8 nt to 1390 nt of the sequence shown in SEQ ID NO. 2 under stringent condition (hybridization condition: in 5×SSC, 50% formamide, 0.1% SDS at 42° C. for 12 hours; washing condition: 0.1×SSC, 0.1% SDS, 68° C., 15 min.) may be employed as long as the polypeptide encoded thereby has phytase activity.

The recombinant vector employed in the present invention may be constructed by inserting the above-mentioned promoter and the above-mentioned gene encoding the polypeptide having phytase activity at a site downstream of the promoter, which gene is operably linked to the promoter, into a vector which can replicate in the host *Candida boidinii*. As the vector into which the promoter and the gene are to be inserted, commercially available vectors used for transformation of *E. coli,* such as pUC18 and pBR322 may be employed.

The recombinant vector may preferably have a selection marker in order to select the transformed host cells. Examples of the selection marker include genes which influence on the growth of the cells, such as genes related to synthesis of nucleic acids or amino acids, and drug resistant genes. Further, since the recombinant vector of the present invention is retained in the transformed host cells, the recombinant vector preferably has a sequence which enables the vector self-replicating in the host cell or a sequence having a high homology to a sequence in a chromosomal DNA in the host cell in order that the vector or a fragment thereof may be inserted into the chromosomal DNA by homologous recombination. Still further, in order to promote expression efficiency, it is preferred that the recombinant vector have a terminator at a site downstream of the gene encoding the polypeptide having phytase activity. A preferred example of the terminator is the terminator of AOD1 gene of *Candida boidinii.*

Figure 2:
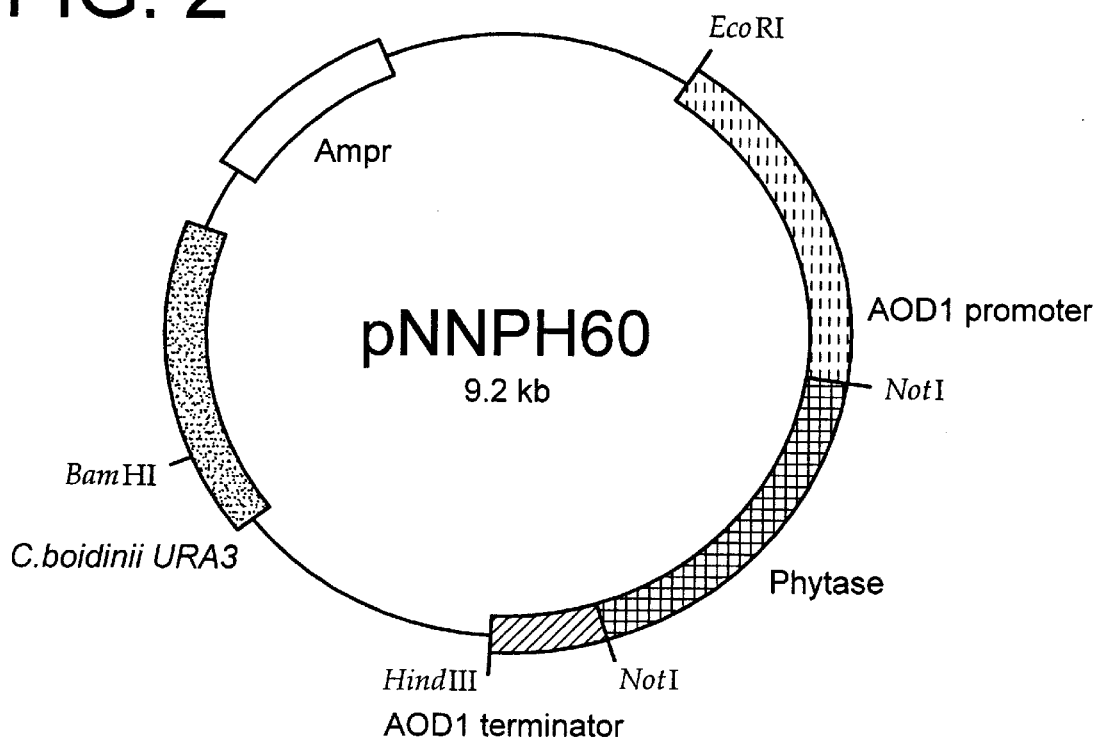
FIG. 2 shows the structure of a recombinant plasmid pNNPH60 for expressing the phytase gene originated from *Schwaniiomyces occidentalis* in host *Candida boidinii.

A preferred example of such a recombinant vector is pNNPH60 shown in FIG. 2 prepared in the actual working example described below, which comprises the promoter of AOD1 gene of *Candida boidinii* and the phytase gene of *Schwanniomyces occidentalis* ligated to a downstream site of the promoter.

The host transformed with the recombinant vector according to the present invention is *Candida boidinii.* The host *Candida boidinii* may be transformed with the recombinant vector by a method well-known in the art.

The desired polypeptide having phytase activity may be secretionary produced by culturing the obtained recombinant *Candida boidinii* in a specific liquid culture medium hereinbelow described in detail while adding methanol. The culturing conditions will now be described in detail.

The liquid medium employed in the method of the present invention is an aqueous medium containing an assimilable carbon source, nitrogen source, inorganic salts and trace amounts of organic and inorganic components in amounts by which the yeast cells are sustained and the desired polypeptide is produced. The medium may be synthetic or natural.

Methanol is an inducer and simultaneously is a carbon source. However, the carbon source added to the liquid medium at the beginning of the culture is not restricted to methanol, and any carbon source with which the yeast can grow sufficiently in a short time may be employed. Examples of such a carbon source include those which function only as a carbon source such as glycerol, glucose, sucrose, organic acids, as well as those which function not only as the carbon source but also as the nitrogen source or phosphorus source, such as molasses, peptone, yeast extract, corn step liquor and meat extract. These carbon sources may be employed individually or in combination. Further, methanol may be added together with one or more of the above-mentioned carbon sources.

Examples of the nitrogen source include ammonia, urea and ammonium salts such as ammonium chloride, ammonium sulfate, ammonium acetate, ammonium phosphate and ammonium nitrate.

Examples of the inorganic salts include potassium dihydrogen phosphate, dipotassium hydrogen phosphate, sodium chloride, magnesium sulfate, calcium chloride, zinc sulfate, copper sulfate, ferrous sulfate and the like. Such inorganic salts may be added as required. Further, trace components including vitamins such as thiamin hydrochloride and biotin may also be added as required. The liquid medium containing an assimilable carbon source, nitrogen source, inorganic salts and trace amounts of organic and inorganic components in amounts by which the yeast cells are sustained and the desired polypeptide is produced is well-known in the art.

In the method of the present invention, the liquid medium contains phosphoric acid or a phosphate compound in an amount effective of restricting the growth of *Candida boidinii*, that is, in an amount that the phosphoric acid or the phosphate compound serves as a limiting factor to the growth of the cells. In this sense, the above-mentioned components of the liquid medium other than the phosphoric acid and the phosphate compounds should be added sufficiently such that the components do not run short during the entire culture time. Whether the amount of the phosphoric acid or the phosphate compound serves as the limiting factor may be easily judged by checking whether the growth of the cells is promoted by addition of phosphoric acid or the phosphate compound.

Examples of the phosphate compound which may be employed include inorganic phosphate salts such as ammonium phosphate, potassium phosphate, sodium phosphate calcium phosphate and the like, as well as organic phosphates in components contained in natural media, which components are originated from organisms. Preferred concentration of the phosphoric acid or the phosphate compound varies depending on the final concentration of the cells aimed at, and usually 0.3–3 g/l, preferably 0.5–2.0 g/l in terms of phosphate group, in view of assuring a degree of secretionary production of the polypeptide and of avoiding excess proliferation of the cells.

In the method of the present invention, the above-mentioned recombinant *Candida boidinii* is inoculated to the above-mentioned liquid medium and cultured therein. The culture temperature, aeration and stirring conditions, pH of the medium and other conditions may be the ordinary conditions conventionally employed for culturing *Candida boidinii*. Particularly, the culture temperature may preferably be 20–40° C. and the pH of the medium may preferably be 3.0 to 7.0. To efficiently produce the polypeptide having phytase activity, the culture may preferably be continued for not less than 10 days, more preferably not less than 15 days.

After beginning of the culture, with the growth of the recombinant *Candida boidinii*, the carbon source is depleted and the dissolved oxygen level is increased. After reaching this stage, the culture is continued in the presence of nitrogen source while adding methanol and an alkali as a pH regulator alone. Unless the carbon source contained in the medium from the beginning of the culture is not one hardly assimilated, the time point at which addition of methanol is commenced after depletion of the carbon source is usually 24–96 hours from the beginning of the culture. In cases where sufficient amount of nitrogen source is contained in the medium from the beginning of the culture, a solution of a caustic alkali such as sodium hydroxide or potassium hydroxide may be employed as the pH regulator. However, usually, aqueous ammonia or ammonia gas, which also serves as the nitrogen source, is added to regulate pH.

By continuing the culture while adding methanol, increase in the concentration of the cells is substantially stopped because the amount of phosphoric acid or the phosphate compound acts as the limiting factor. Here, the state in which the concentration of the yeast cells is not substantially increased means the state that the amount of the yeast cells is not increased to a level not less than twice within one week.

By keeping the rate of addition of methanol, the secretion of the polypeptide having phytase activity is continued linearly with respect to time. In view of the production efficiency suited for commercial production, the cell concentration may preferably be 5 g/l to 120 g/l, preferably 10 g/l to 80 g/l in terms of dry weight of the cells. If the cell concentration is less than 5 g/l, the production efficiency of the polypeptide is low. If the cell concentration is more than 120 g/l, the components of the medium are wasted for the proliferation of the cells, the purification of the produced polypeptide is troublesome and the cost for disposing the used yeast cells is large.

Further, as mentioned above, since *Candida boidinii* secretes a kind of polysaccharide, if the cell concentration in the medium is too high, the polysaccharide is accumulated in the medium and the viscosity of the culture medium is increased. As a result, the supply oxygen to the yeast cells is difficult, so that the production efficiency of the desired recombinant polypeptide is low.

Methanol may be added to the liquid medium continuously or intermittently. In this case, if a large amount of methanol is added in a short time, production of the desired polypeptide is decreased and in some cases, the cells are killed so that the production of the polypeptide is stopped. Therefore, it is usually preferred to continue the culture while restricting the level of methanol used as the induction substance and as the carbon source to less than 1.0% (v/v).

The methanol level in the culture medium can be determined by subjecting a small amount of the culture medium to gas chromatography. It is a practical method to add methanol while continuously monitoring the methanol level with a methanol sensor. Alternatively, under the conditions wherein the carbon source other than methanol has depleted, depletion of methanol may be continuously monitored by measuring dissolved oxygen level with a dissolved oxygen electrode.

When the culture is continued, the amount of the cells of *Candida boidinii* is not substantially increased or not extremely decreased. This fact that the *Candida boidinii* keeps a cell concentration for a long time is totally unexpected and was discovered by the present inventors.

The end of the culture may be selected depending on the production efficiency of the polypeptide and the production cost. Usually, the culture is ended at about 100 days, preferably about 50 days from the beginning of the culture.

The cells are then removed from the obtained culture medium by centrifugation or the like and the polypeptide having phytase activity may be recovered by a conventional method for recovering proteins. The recovered polypeptide may be further purified. In view of the fact that the polypeptide having phytase activity is useful as an additive of feed of livestock, the crude polypeptide recovered from the culture medium may be the final product, or the polypeptide containing the components of the medium, which do not adversely affect to the livestock, may be the final product.

The invention will now be described more concretely by way of examples thereof. It should be noted, however, the examples are presented for the illustration purpose only and should not be interpreted in any restrictive way. In the Examples, "%" means w/v % unless otherwise specified or unless otherwise clear from the context.

EXAMPLE 1

(1) Construction of Expression Plasmid

A plasmid containing cDNA encoding phytase of *Schwaniiomyces occidentalis*, which cDNA is cloned by using ZAP-cDNA synthesis kit (commercially available from Stratagene), was extracted from *Candida boidinii* MT-10743 (deposited under the Budapest Treaty on Apr. 21, 1994 with National Institute of Bioscience and Human-Technology, Agency of Industrial Science and Technology at 1-3, Higashi 1-chome, Tsukuba-shi, Ibaraki, JAPAN under an accession No. FERM BP-5108), and the extracted plasmid was named pPHY36. The structure of pPHY36 is shown in FIG. 1. In FIG. 1, "Ampr" means ampicillin-resistant gene, and "ori" means replication origin. In pPHY 36, the region originated from a commercial vector pBluescript SK- (commercially available from Stratagene) is 2958 bp and the cDNA of about 1800 bp encoding phytase is inserted between the EcoRI site and the XhoI site. The region also contains a terminator and poly(A) region. The EcoRI site and the NotI site of this plasmid were converted to blunt ends with T4 polymerase and the resultant was ligated with a linker (commercially available from TAKARA SHUZO, Kyoto, Japan) having a NotI site to introduce a NotI site. The XhoI site was converted to blunt end with T4 polymerase and the resultant was ligated with a NotI linker to obtain a plasmid having NotI sites a the 5'- and 3'-ends of the cDNA. This plasmid was digested with NotI and the obtained cDNA fragment was ligated to the NotI site of a plasmid pNote I (EP-A-0 558 024) which is an expression plasmid for exogenous protein of *Candida boidinii* to obtain a plasmid pNNPH60. The structure of pNNPH60 is shown in FIG. 2. In FIG. 2, "Ampr" means ampicillin-resistant gene, and "C.boidinii URA3" means the URA3 gene originated from *Candida boidinii*.

(2) Transformation

*Candida boidinii* TK62 described in EP-A-0 558 024 was inoculated to 5 ml of YPD medium (1% yeast extract, 2% polypeptone, 2% glucose) and cultured under shaking at 28° C. for 30 hours to obtain a preculture medium. The obtained preculture medium was inoculated to 100 ml of YPD medium to a concentration that the optical density at 610 nm ($OD_{610}$) is 0.2, and the resulting culture medium was cultured for about 12 hours at 28° C. until $OD_{610}$ reached about 1.0. Cells in the resulting culture medium was collected and suspended in 25 ml of lithium-containing solution (10 mM Tris-HCl (pH 8.0), 1 mM EDTA, 3 mM lithium acetate). The cells were then collected by centrifugation and suspended again in 5 ml of the lithium-containing solution, followed by incubating the resulting suspension at 30° C. for 1 hour under shaking to convert the cells to competent cells. In a 1.5 ml tube, 10 µl of 10 µg/µl thermally denatured calf thymus solution, 5 µl of 1 µg/µl pNNPH60 digested with BamHI and 100 µl of the competent cell suspension were placed and the resultant was gently mixed, followed by static incubation of the resultant at 30° C. for 30 minutes. Thereafter, 700 µl of 45% PEG solution (45% (w/v) polyethylene glycol #4000 (PEG), 10 mM Tris-HCl (pH 8.0), 1 mM EDTA, 3 mM lithium acetate) was added and the resultant was gently mixed, followed by static incubation at 30° C. for 1 hour. Thereafter, the culture medium was subjected to heat shock at 42° C. for 5 minutes and the resultant was left to stand at 30° C. for 5 minutes. After collecting the cells by centrifugation, the cells were suspended in 1 ml of sterilized water and aliquots thereof with a volume of 200 µl each was applied to YNB plates (0.67% Yeast Nitrogen base w/o Amino acid (commercially available from Difco), 2% glucose, 2% agar) and the YNB plates were cultured at 28° C. for 3 days. By this operation, only transformed cells formed colonies.

(3) Screening of Strains Highly Producing Phytase

To select the strains highly producing the phytase originating from *Schwaniiomyces occidentalis* from the *Candida boidinii* transformants obtained in Section (2), the following culture was carried out and the phytase activities in the culture supernatants were compared.

That is, each single colony was precultured in 5 ml of YPD medium at 28° C. for 24 hours. The obtained preculture medium was inoculated to 20 ml of YPGM medium (1% yeast extract, 2% polypeptone, 3% glycerol, 1.5% methanol) to a concentration attaining $OD_{610}$ of 0.2, and the resultant was cultured at 28° C. for 3 hours, followed by centrifugation of the resultant to obtain supernatant containing phytase. The supernatant was 10-fold concentrated by ultrafiltration and the medium components were replaced with ion-exchanged water. The phytase solution was concentrated or diluted to the concentration suited for the enzyme reaction and 900 µl of 60 mM sodium acetate buffer (pH 4.2) containing 5 mM of sodium phytate was added to 100 µl of the enzyme solution, followed by carrying out the reaction at 70° C. for 30 minutes. After the reaction, 100 µl of 5N sulfuric acid was added to the reaction solution to stop the reaction. As a control, a solution containing the substrate in a buffer to which 100 µl of 5N sulfuric acid and the enzyme solution were added was used. After the reaction, the reaction mixture was appropriately diluted and the amount of the generated phosphate was measured by colorimetric measurement by the method of Heinonen and Lahti (Anal. Biochem., Vol. 113, pp.313–317, (1981)).

The amount of the produced phytase was calculated based on the calculation that 1 mg of phytase catalyzes the reaction by which 320 µmol of phosphate is liberated each minute. By this procedure, transformants having various productivities of phytase were obtained. Among the transformants, a strain showing high production of phytase was obtained and named MT-40544. This strain was deposited under the Budapest Treaty on May 31, 1996 with National Institute of Bioscience and Human-Technology, Agency of Industrial Science and Technology at 1-3, Higashi 1-chome, Tsukuba-shi, Ibaraki, JAPAN under an accession No. FERM BP-5936.

EXAMPLE 2

Secretionary Production of Phytase (1)

The transformant MT-40544 obtained in Example 1 was cultured by the following method:

That is, 100 ml of a medium containing 1% corn steep liquor, 0.5% ammonium sulfate, 0.1% dipotassium hydrogen phosphate and 2% glucose was placed in a 500 ml Erlenmeyer flask with a buffle and sterilized at 121° C. for 20 minutes. To this medium, one platinum loop of MT-40544 was inoculated and cultured under shaking at 28° C. for 24 hours. Then 1200 ml of a medium (0.5% yeast extract (containing 3.3% phosphate group), 3% glycerol, 0.5% ammonium sulfate, 0.2% potassium dihydrogen phosphate and 0.1% magnesium sulfate heptahydrate) was placed in a jar fermenter with a volume of 21 times and was sterilized. Then 18 ml of methanol was added and the entire preculture medium described above was added. The resultant was cultured at 28° C., at an aeration rate of 1.0 vvm, at 700 rpm of stirring blade and at a pH of 5.5 adjusted with 5% aqueous ammonia.

After beginning of the culture, the dissolved oxygen level once decreased to 0% and then begun to increase. At 60 hours from the beginning of the increase in the dissolved oxygen level, methanol was begun to be added and thereafter, only methanol and aqueous ammonia as a pH regulator were added. The dissolved oxygen level was monitored and methanol was added when the dissolved oxygen level reached to 30% of saturation. Although methanol was added at a rate of about 1 g/l/h, since water was not recovered from the waste gas from the jar fermenter, the volume of the culture medium was substantially kept constant throughout the entire period of the culture.

Figure 3:
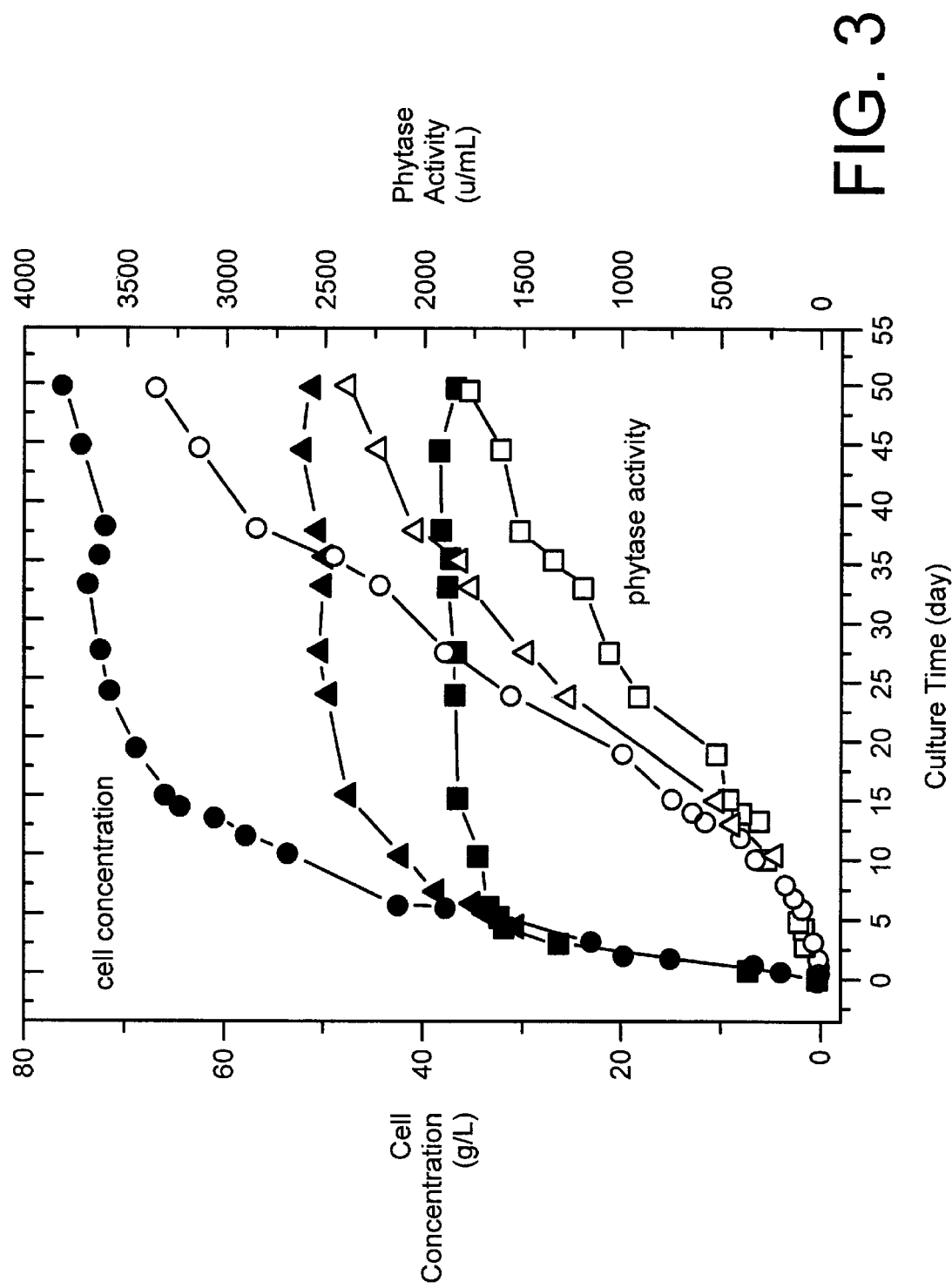
* and FIG. 3 shows changes in time of the amounts of the cells and phytase activities, when a transformant yeast MT-40544 is cultured while adding methanol under different phosphate concentrations.

The results are shown in FIG. 3 as the circle symbols. The painted circle symbols indicate the cell concentration and the hollow circle symbols indicate the phytase activity. As shown, secretionary production of phytase was continued for 50 days from the beginning of the culture keeping the state in which the amount of the cells (dry weight of the cells) is not substantially increased.

EXAMPLE 3

Secretionary Production of Phytase (2)

The same operation as in Example 2 was repeated except that the concentration of potassium dihydrogen phosphate was 0.1% or 0.05% (w/v).

The results are shown in FIG. 3 as square (0.05%) and triangle (0.1% ) symbols. The painted symbols indicate the cell concentrations and the hollow symbols indicate the phytase activities. As shown, profiles with respect to time, similar to that obtained in Example 2, were obtained, even though the finally reached cell concentrations and phytase activities are different. Thus, it was proved that secretionary production of phytase can be continued keeping the state in which the amount of the cells is not substantially increased utilizing the amount of phosphate group in the culture medium as a growth-limiting factor.

We claim:

1. A method for continuously producing a polypeptide having phytase activity, comprising (i) obtaining *Candida boidinii* cells which have been transformed with a recombinant vector comprising a methanol inducible promoter and a DNA sequence encoding polypeptide having phytase activity operably linked to the downstream of said promoter, (ii) culturing, by fermentation, said cells in a liquid culture medium containing methanol and further containing an amount of phosphoric acid or a phosphate compound sufficient to restrict cell proliferation, (iii) maintaining continuously the expression and secretion of said polypeptide by the continued addition of methanol and by maintaining the state of the culture such that it comprises an amount of phosphoric acid or a phosphate compound sufficient to restrict cell proliferation such that the number of said cells is not substantially increased, and (iv) isolating the expressed polypeptide from culture medium.

2. The method according to claim 1, wherein said promoter is the alcohol oxidase 1 gene promoter of *Candida Boidinii*.

3. The method according to claim 1, wherein said phosphoric acid or phosphate compound is contained in said liquid medium in an amount of 0.3 to 3.0 g/l in terms of phosphate group.

4. The method according to claim 1, wherein the culturing is continued for not less than 10 days.

5. The method according to claim 4, wherein said polypeptide having phytase activity is phytase of *Schwanniomyces occidentalis*.

6. The method according to claim 2, wherein said polypeptide having phytase activity is phytase of *Schwanniomyces occidentalis*.

7. The method according to claim 3, wherein said polypeptide having phytase activity is phytase of *Schwanniomyces occidentalis*.

8. The method according to claim 1, wherein said polypeptide having phytase activity is phytase of *Schwanniomyces occidentalis*.

9. The method according to claim 5, wherein said *Candida boidinii* transformant is MT-40544 (FERM BP-5936).

10. The method according to claim 6, wherein said *Candida boidinii* transformant is MT-40544 (FERM BP-5936).

11. The method according to claim 7, wherein said *Candida boidinii* transformant is MT-40544 (FERM BP-5936).

12. The method according to claim 8, wherein said *Candida boidinii* transformant is MT-40544 (FERM BP-5936).

* * * * *